United States Patent
Bausch et al.

(10) Patent No.: US 8,273,798 B2
(45) Date of Patent: Sep. 25, 2012

(54) TAMPER RESISTANT LIPID-BASED ORAL DOSAGE FORM FOR OPIOID AGONISTS

(75) Inventors: James M. Bausch, Wildwood, MO (US); Alvin Kershman, Paradise Valley, MO (US); Jeff L. Shear, Chesterfield, MO (US); Linda L. Lewis, Pacific, MO (US)

(73) Assignee: Shear Kershman Laboratories, Chesterfield, MO (US)

( * ) Notice: Subject to any disclaimer, the term of this patent is extended or adjusted under 35 U.S.C. 154(b) by 250 days.

(21) Appl. No.: 12/156,775

(22) Filed: Jun. 4, 2008

(65) Prior Publication Data

US 2009/0076177 A1 Mar. 19, 2009

Related U.S. Application Data

(60) Provisional application No. 60/933,031, filed on Jun. 4, 2007.

(51) Int. Cl.
*A61K 9/00* (2006.01)
*A61K 47/00* (2006.01)
(52) U.S. Cl. ........................................ 514/785; 424/498
(58) Field of Classification Search .................. None
See application file for complete search history.

(56) References Cited

U.S. PATENT DOCUMENTS

| | | | |
|---|---|---|---|
| 3,980,766 A | 9/1976 | Shaw et al. | |
| 4,070,494 A | 1/1978 | Hoffmeister et al. | |
| 6,136,864 A | 10/2000 | Nichols et al. | |
| 6,197,314 B1 | 3/2001 | Einig | |
| 6,251,430 B1 | 6/2001 | Zhang et al. | |
| 6,309,668 B1 * | 10/2001 | Bastin et al. | 424/472 |
| 6,375,957 B1 | 4/2002 | Kaiko et al. | |
| 6,419,954 B1 * | 7/2002 | Chu et al. | 424/465 |
| 6,709,669 B1 * | 3/2004 | Murray et al. | 424/434 |
| 7,332,182 B2 | 2/2008 | Sackler | |
| 2002/0082304 A1 | 6/2002 | Bess et al. | |
| 2003/0049315 A1 * | 3/2003 | Daggy et al. | 424/465 |
| 2003/0068375 A1 | 4/2003 | Wright et al. | |
| 2003/0068392 A1 * | 4/2003 | Sackler | 424/760 |
| 2005/0281748 A1 | 12/2005 | Hirsch et al. | |
| 2007/0014732 A1 | 1/2007 | Sackler | |
| 2007/0026074 A1 * | 2/2007 | Martin et al. | 424/488 |

FOREIGN PATENT DOCUMENTS

| WO | 03/013479 | * | 2/2003 |
|---|---|---|---|
| WO | WO 03013479 A1 | * | 2/2003 |

OTHER PUBLICATIONS

Pornsak Sriamornsak and Srisagul Sungthongjeen. Modification of Theophylline Release With Alginate Gel Formed in Hard Capsules. AAPS PharmSciTech. 2007; 8(3): Article 51 E1-E8.*
Sriamornsak P, Sungthongjeen S. Modification of Theophylline Release With Alginate Gel Formed in Hard Capsules. AAPS PharmSciTech. 2007; 8(3): Article 51 E1-E8.*
Demirturk et al. In Vivo—In Vitro Correlations. FABAD J. Pharm/Sci. 28, 215-224, 2003.*
Jaber Emami. In vitro—In vivo Correlation: From Theory to Applications. J Pharm Pharmaceut Sci (www.cspscanada.org) 9(2):169-189, 2006.*

* cited by examiner

*Primary Examiner* — Robert A Wax
*Assistant Examiner* — Olga V Tcherkasskaya
(74) *Attorney, Agent, or Firm* — CreatiVenture Law LLC; Linda L. Lewis

(57) ABSTRACT

A tamper resistant drug delivery system made of at least one lipid, at least one gelling agent and at least one drug active, such as oxycodone, where the system gels rapidly in the presence of water or a solution containing water, and the drug active releases into the digestive system, wherein the weight ratio of gelling agent to lipid is less than 1:1.4.

20 Claims, No Drawings

TAMPER RESISTANT LIPID-BASED ORAL DOSAGE FORM FOR OPIOID AGONISTS

RELATED APPLICATIONS

This applications claims the benefit of provisional application 60/933,031 filed Jun. 4, 2007.

FIELD OF THE INVENTION

The field of the invention is oral dosage forms of opioids. More specifically, the field is lipid-based oral dosage optionally combined with a gelling agent for opioid agonists that are tamper-resistant and are not easily abused. The dosage form cannot be crushed to provide the opioid for immediate release upon oral, parental or nasal administration. Neither can the opioid agonist be easily extracted by the cold water extraction method of separation. While being abuse-resistant, the dosage form also effectively releases into the digestive system when ingested.

BACKGROUND OF THE INVENTION

Opioids are sometimes the subject of abuse. An opioid dosage can be concentrated in a solution to be consumed by oral ingestion, by injection, or transmucally via the anus. In a tablet form, it can be crushed into a powder for snorting (nasally).

A number of opioids are combination drugs containing not only an opioid such as oxycodone, but also an analgesic such as acetaminophen. To abuse these combination drugs, it is necessary for the abuser to separate out the acetaminophen before concentrating the opioid, because high dosages of this analgesic can cause liver damage. The separation method is called "cold water extraction," and it uses the differences in solubility of oxycodone and acetaminophen to separate the two actives. The first step of this method is to dissolve multiple dosages in a small amount (5.0 mL) of warm water. The second step is to chill the solution, causing the less-soluble acetaminophen to precipitate out and be removed by filtration. A way of hindering the cold water extraction process is adding a gelling agent to the dosage, so that when water is added to the dosage, a gel is formed which holds the acetaminophen and the oxycodone together. Subsequently, they cannot be separated by filtration.

A number of additional approaches are known in the art for creating tamper-resistant forms of opioids, including using adversive agents (irritants, bitter and sour flavorings), opioid antagonists, opioid quenching agents, and covalently binding the opioid to amino acids.

Tamper-resistant delivery systems using gelling agents in a drug delivery form with the opioid are known in the art. When the dosage is dissolved in a small amount of water, instead of a solution, a viscous gel that cannot be injected may be formed. For combination drug systems, the gel prevents the acetaminophen from being removed by cold water extraction, because the gel retains the drugs together when extraction is attempted. U.S. Pat. Nos. 3,980,766 and 4,070,494 and U.S. patent application publications 2003/0068471, 2003/0068375, and 2007/0014732 disclose the use of gelling agents to create tamper-resistant drug delivery forms.

However, for each of these patents and publications, rapid gelling in combination with release of the opioid from the delivery system when ingested is not demonstrated, with the exception of U.S. Pat. No. 4,070,494. This patent discloses the use of a gelling agent with an opioid, and uses a "tail flick test" with rats to demonstrate release of the opioid. However, such release results are contrary to the data of the present application. Further, publications 2007/0014732 and 2003/0068471 found the use of gelling agents did not adversely affect release of the opioid, but the amount of gel added was very low, from 2.4 to 7.2% of the formula, and, according to their specifications, did not provide rapid gelling at those levels when tested, or gelling at all unless the mixture was heated, then cooled. The other patents and publications did provide gelling agents at a high enough concentration to cause rapid gelling, but did not address the problem of drug release upon ingestion.

The present application discloses that gelling agents can adversely affect the release of the opioid upon ingestion, thereby defeating the usefulness of the medication. However, the combination of an effective amount of gelling agent with a lipid suspension can provide both the desired rapid gelling in the presence of an aqueous solvent and the desired release of the drug in the digestive system.

SUMMARY OF THE INVENTION

The present invention is a lipid-based oral dosage form of one or more opioids that is tamper-resistant, in that the dosage cannot be easily crushed or extracted with an aqueous solvent to recover and concentrate the opioid for abuse. The lipid-based oral dosage contains sufficient lipid in its composition to provide malleability, or fluidity if liquid at room temperature. The lipid-based dosage form contains a gelling agent that rapidly gels in the presence of water or a solution containing water. The gelling agent:lipid weight ratio is less than about 1:1.4, because at higher ratios, the dosage form does not effectively release the drug into the digestive system.

DETAILED DESCRIPTION OF THE INVENTION

The opioid agonists useful in the present invention include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl and derivatives, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papavereturn, pentazocine, phenadoxone, phenomorphan, phenazocine, phenoperidine, piminodine, piritramide, propheptazine, promedol, properidine, propoxyphene, sufentanil, tilidine, tramadol, mixtures of any of the foregoing, salts of any of the foregoing, and the like. In certain embodiments, the amount of the opioid agonist in the claimed opioid composition may be about 75 ng to about 750 mg.

In certain preferred embodiments, the opioid agonist is selected from the group consisting of hydrocodone, morphine, hydromorphone, oxycodone, codeine, levorphanol, meperidine, methadone, oxymorphone, buprenorphine, fentanyl and derivatives thereof, dipipanone, heroin, tramadol, etorphine, dihydroetorphine, butorphanol, levorphanol, or salts thereof or mixtures thereof. In certain preferred embodiments, the opioid agonist is oxycodone or hydrocodone.

Additionally, agents other than opioid analgesics which are subject to abuse may be used in accordance with the present invention in place of the opioid analgesics in the dosage form. Certain agents include, for example and without limitation, analgesics, tranquilizers, CNS depressants, CNS stimulants, sedative hypnotics and the like. More specifically, barbiturates such as phenobarbital, secobarbital, pentobarbital, butabarbital, talbutal, aprobarbital, mephobarbital, butalbital, pharmaceutically acceptable salts thereof, and the like; benzodiazepines such as diazepam, chlordiazepoxide, alprazolam, triazolam, estazolam, clonazepam, flunitrazepam, pharmaceutically acceptable salts thereof, and the like; stimulants such as gamma-hydroxybutyrate, dextroamphetamine, methylphenidate, sibutramine, methylenedioxymethamphetamine, pharmaceutically acceptable salts thereof, and the like; and other agents such as marinol, meprobamate, carisoprodol, and their precursors, such as pseudoephedrine, and pharmaceutically acceptable salts thereof and the like.

Various gelling agents can be employed including, for example and without limitation, sugars or sugar derived alcohols, such as mannitol, sorbitol, and the like, starch and starch derivatives, cellulose derivatives, such as microcrystalline cellulose, sodium caboxymethyl cellulose, methylcellulose, ethyl cellulose, hydroxyethyl cellulose, hydroxypropyl cellulose, and hydroxypropyl methylcellulose, attapulgites, bentonites, dextrins, alginates, carrageenan, gum tragacanth, gum acacia, guar gum, xanthan gum, pectin, gelatin, kaolin, lecithin, magnesium aluminum silicate, the carbomers and carbopols, polyvinylpyrrolidone, polyethylene glycol, polyethylene oxide, polyvinyl alcohol, silicon dioxide, surfactants, mixed surfactant/wetting agent systems, emulsifiers, other polymeric materials, and mixtures thereof, etc. The pectin or pectic substances useful for this invention include not only purified or isolated pectates but also crude natural pectin sources, such as apple, citrus or sugar beet residues which have been subjected, when necessary, to esterification or de-esterification, e.g., by alkali or enzymes. Preferably, the pectins used in this invention are derived from citrus fruits such as lime, lemon, grapefruit, and orange.

A preferred gelling agent is one that gels rapidly in the presence of water, e.g., thickens in about 10 seconds or less. Preferred gelling agents are hyaluronic acid or its salt, carboxymethyl cellulose (CMC), guar gum, and a combination of guar gum and xanthan gum. A commercial source of a combination of guar gum and xanthan gum is TIC Pretested® Action Gum 1144 Powder, sold by TIC GUMS, Inc. This gelling agent gels within 10 seconds of contact with water and is suitable for the present invention. A commercial source of CMC is TIC Pretested® Pre-hydrated® Tricalose® CMC 6000 powder, sold by TIC GUMS, Inc.

In one embodiment of the present invention, the delivery system is a solid lipid suspension. The solid lipids of the present invention may be of animal, vegetable or mineral origin, which are substantially water-insoluble, inert, non-toxic hydrocarbon fats and oils and derivatives thereof, and may comprise any of the commonly commercially available fats or oils approved by the Food & Drug Administration, having melting points in the range of about 90 to 160° F. (32 to 71° C.). The lipid may comprise a vegetable oil base commonly known as hard butter. Hard butters are hydrogenated, press fractionated, or other processed oils that are processed or recombined to have a solid fat index (percent solid fat vs. temperature) similar to that of cocoa butter. A preferred lipid is kalomel. However, other lipids may be used that are relatively hard or solid at room temperature, but melt rapidly in the mouth at a temperature of about 92° to 98° F. (29 to 32° C.) (mouth temperature). The lipid is employed in the amounts within the range of from about 20 to 50%. When present below about 20%, the amount of lipid is not sufficient to completely coat the dry particles.

In a second embodiment of the present invention, the lipid is a liquid. Examples of suitable lipids include tallow, hydrogenated tallow, hydrogenated vegetable oil, almond oil, coconut oil, corn oil, cottonseed oil, light liquid petrolatum, heavy liquid petrolatum, olein, olive oil, palm oil, peanut oil, persic oil, sesame oil, soybean oil or safflower oil. In this embodiment, fatty acids are also considered suitable, such as palmitic acid and linoleic acid.

Additionally, stearines can be used as a lipid in the present invention. The addition of stearines to the solid lipids provides the favorable property of mold-release. Further, the addition of stearines raises the melting point of the composition as high as about 100° F. (38° C.), which is particularly beneficial when the product is shipped or stored in unrefrigerated compartments.

The weight ratio of gelling agent to lipid is critical to the combination of tamper-resistance and drug-release properties of the dosage form. When the weight ratio of gelling agent to lipid is equal to or greater than about 1:1.4, the delivery system gels, but does not release the drug active into the digestive system. When the ratio is less than about 1:1.4, the drug active is released into the digestive system, but when the ratio of gelling agent to lipid is too low, the dosage form does not gel rapidly to retain the drug active. When the ratio is less than about 1:8, rapid gelling does not occur. A preferred range of gelling agent to lipid is from about 1:2 to 1:7. A more preferred range is from about 1:3 to 1:6.

The fillers of the present invention are pharmacologically inert and optionally nutritionally beneficial to humans and animals. Such fillers include cellulose such as microcrystalline cellulose, grain starches such as cornstarch, tapioca, dextrin, sugars and sugar alcohols such as sucrose sorbitol, xylitol, and mannitol. The fillers may include one or more gelling agent. Preferred fillers include non-fat milk powder, whey, grain brans such as oat bran, and fruit and vegetable pulps. Preferred fillers are finely divided and have a preferred average particle size in the range of about 0.10 to 500 microns. The fillers are present in the drug delivery device in a concentration of about 50 to 80%. Optionally, the opioid particles can also serve as filler in the delivery system.

Optionally, an emulsifier or surfactant may be used in the lipid suspension. Any emulsifier or surfactant approved for use in foods by the Food and Drug Administration and having a relatively low HLB value, in the range of about 1 to 3, is suitable for use in the present invention. The appropriate surfactant minimizes the surface tension of the lipid, allowing it to oil wet and encapsulate the non-oil solid particles. Typically, the surfactant is present in the delivery system in the concentration of about 0.1 to 1.0%. Suitable surfactants include alkyl aryl sulfonate, alkyl sulfonates, sulfonated amides or amines, sulfated or sulfonated esters or ethers, alkyl sulfonates, of dioctyl sulfonosuccinate and the like, a hydrated aluminum silicate such as bentonite or kaolin, triglycerol monostearate, triglycerol monoshortening, monodiglyceride propylene glycol, octaglycerol monooleate, octaglycerol monostearate, and decaglycerol decaoleate. A preferred surfactant is lecithin and/or Durfax™ 80, a emulsifier made of sorbitan esters and ethoxylates, sold by Lodas Croklaan.

In a preferred embodiment, the opioid is microencapsulated. Such microencapsulation includes sustained release encapsulation. Any known method of encapsulation is suitable in the present invention. Such methods include, but are not limited to air coating, chemical erosion, coacervation, fluid bed coating, macroencapsulation, microencapsulation, osmosis, pan spray coating, physical erosion, polymer protein conjugate systems, and polymeric microspheres. A preferred method involves slowly blending the drug with a filming agent solution to form granulated particles. The granulated particles are allowed to dry on a tray and are sieved to the desired size, typically in the range of from about 200 to 500 microns. The coating materials include, but are not limited to, acrylic polymers and co-polymers, alginates, calcium stearate, cellulose, including methylcellulose, ethylcellulose, and hydroxypropyl cellulose, gelatins, glyceryl behenate, glycholic acid and its various forms, ion exchange resins, lactic acid and its various forms, lipids, methacrylic monomers, methacrylic polymers and co-polymers, polyethylene glycol polymers, shellac (pharmaceutical glaze), stearic acid, glycerol esters of fatty acids and waxes.

In a second embodiment, the opioid agonist is suspended in the lipid as dry particles, and the resulting dosage form is microencapsulated, so that not only the opioid agonist, but the lipid and other dry particles are microencapsulated. In a third embodiment, the lipid formulation is enclosed in a gel capsule, and the capsule is coated with a coating material for encapsulation.

In another embodiment of the present invention, the opioid agonist is not microencapsulated, but suspended in the lipid as dry particles. Typically the opioid is present in the delivery device in a concentration of 30% or less. However, the opioid can comprise all of the dried particles, to provide the necessary dose.

Optionally, the dry particles include flavorings that make the device taste and smell appealing to humans or animals. The flavorings can be natural or synthetic, and can include fruit flavorings, citrus, meat, chocolate, vanilla, fish, butter, milk, cream, egg or cheese. The flavorings are typically present in the device in the range of about 0.05 to 50.0%.

The delivery device may also include other pharmaceutically acceptable agents, such as additional analgesics, sweetening agents, including hydrogenated starch hydrolysates, synthetic sweeteners such as sorbitol, xylitol, saccharin salts, L-aspartyl-L-phenylalanine methyl ester, as well as coloring agents, other binding agents, lubricants, such as calcium stearate, stearic acid, magnesium stearate, antioxidants such as butylated hydroxy toluene, antiflatuants such as simethicone and the like. Additional agents include protease inhibitors, absorption enhancers and mucoadhesives.

Optionally, rupturing agents (also known as disintegrating agents) are used to rapidly deliver the opioid agonist into the recipient's system. A typical disintegrating agent is a starch that swells in the presence of water. Various modified starches, such as sodium starch glycolate, currently marketed under the trade names EXPLOTAB® or VIVASTAR®, sold by JRS Pharma, are used as disintegrating agents. Another disintegrating agent is croscarmellose sodium, marketed as VIVASOL® also sold by JRS Pharma. When ingested, the capsule or pellet swells in the presence of gastric juices and ruptures.

In one embodiment of the present invention, the rupturing agent is present inside the microcapsule. As water penetrates the microcapsule, it swells the starch and ruptures the capsule, rapidly delivering the peptide to the system. Additional rupturing agents are disclosed in U.S. Pat. No. 5,567,439, which is hereby incorporated by reference.

In another embodiment, the rupturing agent is present in the lipid suspension, which ruptures the dosage, but leaves the microcapsules intact. This allows the delayed delivery of the drug farther along in the digestive system, in the intestines or the colon. The present invention is particularly effective in this embodiment, in that the ingested dosage may be chewable, where the dosage cleaves in the lipid suspension when chewed, but leaves the microcapsules intact. Tablets or gel capsules, when chewed, typically result in damage to or rupturing of the microcapsules defeating the effectiveness of the microcapsules.

In yet another embodiment, multiple drugs have multiple encapsulations, each containing a rupturing agent. The filming agents used for encapsulation are selected to disintegrate at selected pH conditions, which rupture and release each opioid agonist at desired locations in the digestive system. In another embodiment, the use of a mucoadhesive could effect the delivery of the opioid to the colon.

The process for preparing the above delivery system comprises melting the lipid and mixing with the surfactant. The dry particles are mixed with the melted lipid mixture to form a suspension which may exhibit pseudoplastic and/or thixotropic flow properties, and poured or molded to provide dosage forms.

The dry particles, which include the opioid agonist, filler and optional flavorings and additives, are pre-blended and typically have a particle size in the range of from about 50 to 450 microns. The pre-blended particles are gradually added to the heated lipid base until a high solid suspension is obtained, typically in the range of about 50 to 80% particles and from about 50 to 20% lipid. The preferred form of opioid is the micronized form.

Slow addition of the dry particles is critical in the production of the device, to insure that the particles are suspended in their micronized state and not as agglomerated clumps. The mixing step is accomplished in a heated mixing device that insures thorough mixing of all materials with minimal shear, such as a planetary mixer or a scrape surface mixer. After the suspension is formed, the product is poured into molds and allowed to cool. De-molding and packaging are then performed. Alternatively, the suspension can be super-cooled and sheeted in a semi-soft format. The sheet is processed through forming rolls containing a design or configuration that embosses and forms the final shape.

Liquid lipid suspensions can be prepared by mixing the opioid, other dry particles and excipients with the liquid lipid. The suspension can be placed in gel capsules as dosage forms.

The following examples are to illustrate the claimed invention and are not intended to limit the claims in any way. All of the percentages are by weight unless otherwise indicated.

CONTROL 1

Solid Dosage Form with no Lipid

Control 1 was a dosage form formulated with Red 40 Lake dye, instead of an opioid, which would allow a visual evaluation of the release properties of the formula. The dry ingredients, below were blended and placed in a gel capsule.

TABLE 1

| Ingredient | Weight % |
| --- | --- |
| Action Gum 1144 (gelling agent) | 20.0 |
| VIVASTAR ® (disintegrating agent) | 38.0 |
| VIVASOL ® (disintegrating agent) | 38.0 |
| Red 40 Lake (red dye) | 4.0 |

The gel capsule was placed in 500 mL of deionized water at 26° C. with stirring. After 10 minutes, only about 10% of the dye had released, demonstrating poor release properties.

CONTROL 2

A Solid Lipid Oral Dosage Form with a Gelling Agent

The Example can be prepared according to the following procedure.

Forming the Suspension

The lipid (kaomel) was heated in a Hobart 5 Quart planetary mixer jacketed with a heating mantle in the range of about 140 to 150° F. (60 to 66° C.) and melted. The surfactant, lecithin, was added to the lipid with mixing, and the mixture was allowed to cool to about 135° F. (58° C.).

The dry particles, including Red 40 Lake (the drug active substitute), CMC 6000 (prehydrated cellulose gum, a gelling agent), Action Gum 1144 (guar gum and xanthan gum, a gelling agent), VIVASTAR (a disintegrating agent), VIVASOL (a disintegrating agent) and Durfax™ 80 (a surfactant), were screened to a particle size in the range of about 200 and 500 microns and dry-blended. The dry particles were slowly added incrementally to the lipid/surfactant mixture with mixing over a period of about 1 hour, and provided a smooth suspension with no lumps or agglomerations. It was cooled to about 70° F. (21° C.) and placed in a gel cap. See Table 2.

Forming a Lipid Suspension with a Gelling Agent Lipid Ratio of 1:1.4

TABLE 2

| Ingredient | Weight % |
|---|---|
| kaomel (lipid) | 35.0 |
| lecithin (surfactant) | 1.0 |
| Red 40 Lake (the active substitute) | 2.0 |
| Action Gum 1144 (the gelling agent) | 12.5 |
| CMC 6000 (gelling agent) | 12.5 |
| VIVASTAR (disintegrating agent) | 15.0 |
| VIVASOL (disintegrating agent) | 15.0 |
| Durfax ™ 80 (surfactant) | 5.0 |

The formula of Control 2 was prepared with red 40 lake as a drug active substitute. When the dose was crushed, the lipid suspension was deformed, but not crushed into a powder, since the lipid was malleable. The deformed lipid suspension could not be drawn into a syringe for injection. When mixed with water, a gel rapidly formed, which prevented water extraction of the drug active.

Control 2 was placed in a gel cap and added to 500 mL of water at 37° C. with stirring, but only partially released after 10 minutes. With gelling agent to lipid weight ratio of 25:35 (or 1:1.4), it appeared that the amount of gelling agent was too high.

EXAMPLE 1

A Lipid Suspension with a Gelling Agent Lipid Ratio of 1:4.5

A lipid suspension was prepared according to the method given for Control 2. See Table 3.

TABLE 3

| Ingredient | Weight % |
|---|---|
| kaomel (lipid) | 45.0 |
| lecithin (surfactant) | 1.0 |
| Red 40 Lake (the active substitute) | 2.0 |
| Action Gum 1144 (the gelling agent) | 10.0 |
| CMC 6000 (gelling agent) | — |
| VIVASTAR (disintegrating agent) | 20.0 |
| VIVASOL (disintegrating agent) | 20.0 |
| Durfax ™ 80 (surfactant) | 3.00 |

The lipid suspension of Example 1 had favorable properties of malleability and tamper-resistance. When wet with 5 mL of water, it gelled and proved resistant to water extraction.

The lipid suspension of Example 1 was placed in a gel cap, and placed in 500 mL water at 37° C., where it readily dissolved, and released the red dye in about 10 minutes. The gelling agent:lipid weight ratio of 10:45 (1:4.5) with less gelling agent than Control 2, and was more conducive to release the drug active, while retaining tamper-resistant properties.

What is claimed is:

1. A tamper-resistant drug delivery system comprising at least one lipid, at least one gelling agent and at least one drug active, wherein the gelling agent rapidly gels in the presence of water in about 10 seconds or less, wherein the drug active releases into the digestive system in about 10 minutes or less, wherein the weight ratio of gelling agent to lipid is less than 1:1.4, wherein the lipid is not a fatty acid, and wherein the lipid is present in the delivery system from about 20 wt. % to 50 wt. %.

2. The drug delivery system of claim 1, wherein the weight ratio of gelling agent to lipid is in the range of from 1:2 to 1:7.

3. The drug delivery system of claim 1, wherein the weight ratio of gelling agent to lipid is in the range of from 1:3 to 1:6.

4. The drug delivery system of claim 1, wherein the system contains at least one disintegrating agent.

5. The drug delivery system of claim 1, wherein the system contains at least one surfactant.

6. The drug delivery system of claim 1, wherein the drug active includes an opioid.

7. A tamper-resistant drug delivery system comprising at least one lipid, at least one gelling agent and at least one drug active, wherein the gelling agent rapidly gels in about 10 seconds or less in the presence of water, and the drug active releases into the digestive system in about 10 minutes or less, and wherein the weight ratio of gelling agent to lipid is less than 1:1.4, wherein the system contains at least one disintegrating agent and at least one surfactant, wherein the drug active includes an opioid, wherein the lipid is not a fatty acid, and wherein the lipid is present in the delivery system from about 20 wt. % to 50 wt. %.

8. The drug delivery system of claim 7, wherein the drug active is microencapsulated.

9. The drug delivery system of claim 7, wherein the lipid is a solid at room temperature.

10. The drug delivery system of claim 7, wherein the lipid is a liquid at room temperature.

11. The drug delivery system of claim 1, wherein the at least one gelling agent is selected from the group consisting of hyaluronic acid, a salt of hyaluronic acid, carboxymethyl cellulose, guar gum, and a combination of guar gum and xanthan gum.

12. The drug delivery system of claim 7, wherein the at least one gelling agent is selected from the group consisting of hyaluronic acid, a salt of hyaluronic acid, carboxymethyl cellulose, guar gum, and a combination of guar gum and xanthan gum.

13. The drug delivery system of claim 1, wherein the lipid is a solid at room temperature.

14. The drug delivery system of claim 1, wherein the drug active is a pharmaceutically acceptable salt.

15. The drug delivery system of claim 7, wherein the drug active is a pharmaceutically acceptable salt.

16. A solid tamper-resistant drug delivery system comprising at least one lipid, at least one gelling agent and the pharmaceutically acceptable salt of at least one drug active, wherein the gelling agent rapidly gels in about 10 seconds or less in the presence of water, and the drug active releases into the digestive system in about 10 minutes or less, and wherein the weight ratio of gelling agent to lipid is less than 1:1.4, wherein the system contains at least one disintegrating agent; and at least one surfactant, wherein the lipid is not a fatty acid, and wherein the lipid is present in the delivery system from about 20 wt. % to 50 wt. %.

17. The drug delivery system of claim 16, wherein at least one drug active includes an opioid.

18. The drug delivery system of claim 16, wherein the at least one gelling agent is selected from the group consisting of hyaluronic acid, a salt of hyaluronic acid, carboxymethyl cellulose, guar gum, and a combination of guar gum and xanthan gum.

19. The drug delivery system of claim 17, wherein the at least one gelling agent is selected from the group consisting of hyaluronic acid, a salt of hyaluronic acid, carboxymethyl cellulose, guar gum, and a combination of guar gum and xanthan gum.

20. The drug delivery system of claim 13, wherein the drug active is a pharmaceutically acceptable salt.

\* \* \* \* \*